(12) United States Patent
Marple et al.

(10) Patent No.: US 6,647,758 B2
(45) Date of Patent: Nov. 18, 2003

(54) METHOD AND APPARATUS FOR VERIFYING INTEGRITY OF CASCADE IMPACTORS

(75) Inventors: Virgil A. Marple, Maple Plaine, MN (US); Daryl L. Roberts, Blaine, MN (US)

(73) Assignee: MSP Corporation, Minneapolis, MN (US)

( * ) Notice: Subject to any disclaimer, the term of this patent is extended or adjusted under 35 U.S.C. 154(b) by 109 days.

(21) Appl. No.: 09/733,106

(22) Filed: Dec. 8, 2000

(65) Prior Publication Data

US 2001/0013244 A1 Aug. 16, 2001

Related U.S. Application Data

(63) Continuation-in-part of application No. 09/679,936, filed on Oct. 5, 2000, and a continuation-in-part of application No. 09/360,466, filed on Jul. 23, 1999, now Pat. No. 6,431,014.

(51) Int. Cl.[7] .............................. G01N 1/12; G01N 1/22; G01N 15/02
(52) U.S. Cl. .................. 73/28.03; 73/863.22; 73/28.05; 73/1.06; 73/37
(58) Field of Search .......................... 73/28.03, 863.22, 73/865.5, 28.05, 28.06, 28.04, 12.01, 12.08, 1.06, 1.02, 37, 38

(56) References Cited

U.S. PATENT DOCUMENTS

| | | | |
|---|---|---|---|
| 3,127,763 A | 7/1961 | Lippmann | |
| 3,001,914 A | 9/1961 | Andersen | 73/28.05 X |
| 3,518,815 A | 7/1970 | McFarland et al. | 55/241 |
| 3,693,457 A | 9/1972 | Pilat | |
| 3,901,798 A | 8/1975 | Peterson | 209/143 |
| 3,922,905 A * | 12/1975 | Rotz | 73/28.04 |
| 3,983,743 A * | 10/1976 | Olin et al. | 73/28.06 |
| 4,133,202 A | 1/1979 | Marple | |
| 4,189,937 A | 2/1980 | Nelson | 73/28.06 |
| 4,211,116 A | 7/1980 | Pilat et al. | 73/853.22 |
| 4,321,822 A * | 3/1982 | Marple et al. | 73/863.22 X |
| 4,387,603 A * | 6/1983 | Nelson | 73/863.22 |
| 4,452,068 A | 6/1984 | Loo | 73/28 |
| 4,463,595 A | 8/1984 | Yeh et al. | 73/863.33 |
| 4,554,051 A | 11/1985 | Danforth | 162/49 |
| 4,570,494 A | 2/1986 | Dunn et al. | 73/863.22 |
| 4,640,140 A * | 2/1987 | Burghoffer et al. | 73/863.22 |
| 4,670,135 A | 6/1987 | Marple et al. | 509/143 |
| 4,764,186 A | 8/1988 | Langer | 55/17 |
| 4,827,779 A * | 5/1989 | Marple et al. | 73/863.22 |
| 4,972,957 A | 11/1990 | Liu et al. | 209/143 |
| 5,040,424 A | 8/1991 | Marple et al. | 73/863.22 |
| 5,201,231 A | 4/1993 | Smith | 73/863.22 |
| 5,323,657 A | 6/1994 | Vander Heyden | 73/861.02 |
| 5,343,767 A | 9/1994 | Marple et al. | 73/863.22 |
| 5,437,198 A | 8/1995 | John | 73/863.22 |
| 6,453,758 B1 * | 9/2002 | Marple et al. | 73/863.22 |
| 2002/0069691 A1 * | 6/2002 | Roberts et al. | 73/46 |

FOREIGN PATENT DOCUMENTS

GB 2351155 A * 12/2000 .......... G01N/15/02

* cited by examiner

*Primary Examiner*—Thomas P. Noland
(74) *Attorney, Agent, or Firm*—Westman, Champlin & Kelly, P.A.

(57) ABSTRACT

An impactor assembly comprises a base for supporting a plurality of cups that form impactor plates, and a nozzle above each of the cups through which a flow passes for classification. The cover is removable, and a test cover can be put into position for mounting in place and providing outlets connectable to pressure sensor for determining pressure drop across the nozzle plates at each impactor stage. The cover also is designed to be easily washed by having no blind cavities or moving parts on the cover, and the latch and other hinge assemblies are all supported on the base. The flow enters and exits the impactor without having external connections on the cover.

6 Claims, 13 Drawing Sheets

METHOD AND APPARATUS FOR VERIFYING INTEGRITY OF CASCADE IMPACTORS

CROSS REFERENCE TO RELATED APPLICATION

This application is a Continuation-in-Part of U.S. patent application Ser. No. 09/360,466, filed Jul. 23, 1999 for HIGH ACCURACY AEROSOL IMPACTOR AND MONITOR, now U.S. Pat. No. 6, 431,014 and also is a Continuation-in-Part of U.S. patent application Ser. No. 09/679,936, filed Oct. 5, 2000, for METHOD AND APPARATUS FOR CASCADE IMPACTOR TESTING, both of which applications are incorporated herein by reference.

BACKGROUND OF THE INVENTION

The present invention relates to improvements to a generally flat side by side cascade impactor, and includes apparatus for testing the integrity of seals, as well as the pressure drop across impactor nozzles or orifice to check the condition of the impactor nozzles. The cascade impactor also includes improvements in mounting and operational features.

In the prior art, it has been known to size classify and collect aerosol particles onto impactor plates. When series arranged nozzles are used, it is desirable to determine the condition of the nozzles, and whether or not they are becoming plugged or worn. This can be done by determining the pressure drop across nozzles, and in a cascade impactor, checking the pressure drop from the inlet to the outlet for total flow analysis is desirable.

Cascade impactors are widely used for size distribution analysis of aerosol particles, for example, for checking for air pollutants, and for also analyzing the chemical makeup of particles in the atmosphere. Size distribution is important, particularly in the drug delivery industry, where a metered dose of an inhaled drug delivered in aerosol form is tested for particle distribution. In such a cascade impactor it is important to insure the consistency of the test, which is related directly to the size of the nozzle or orifice or openings. The total nozzle or orifice opening in a nozzle or orifice plate can be analyzed by determining the pressure drop at a standard flow rate.

SUMMARY OF THE INVENTION

The present invention relates to a drug metered dose or dry powder inhaler cascade impactor that has a separate test cover that can be used for determining the pressure drop across individual impactor nozzles, to in turn determine the condition of the nozzles and whether or not there is any plugging, wear or other abnormality. The separate test cover fits in place on the impactor, and when a standard flow rate of a gas, such as air, is passed through the impactor, the pressure drop across the individual nozzles can be sensed, and the total pressure drop also can be sensed.

The pressure inputs are provided to a set of pressure transducers, that provide outputs indicating pressure in each of the passageways on opposite sides of each nozzle plate, and thus the pressure drop across one or more of the nozzle plates or total pressure drop can be determined easily. The pressure drop can be used for determining an accurate total flow rate, which is important in the determination of particle distribution, particularly in dry powder inhalers.

The test cover that is utilized can also be used for applying a vacuum to the system utilizing a vacuum source, which indicates the integrity of the seals on the individual impaction chambers used in the cascade impactor.

Mechanical improvements shown include the placing of the hinges and latch part devices that have cavities on the base plate only, so that the cover, which has passageways for conducting samples can be washed fully between sample runs in automatic washers. The base that is used is not washed each time, and the parts that have hard to clean bores or recesses located on the base.

Additionally, a unique latch actuator is utilized that will release the latches using a cam arrangement. Further, the cover is made so it can be quickly removed and replaced. The hinges are constructed so the cover will not close if the cover is not properly positioned relative to the base.

A method of milling undercut seal grooves in a seal carrying plate, which are within the boundaries of the plate and do not open to edges where a tool can be introduced is shown. Also, a final filter for the exhaust air is disclosed.

DETAILED DESCRIPTION OF THE PREFERRED EMBODIMENTS

Figure 16:
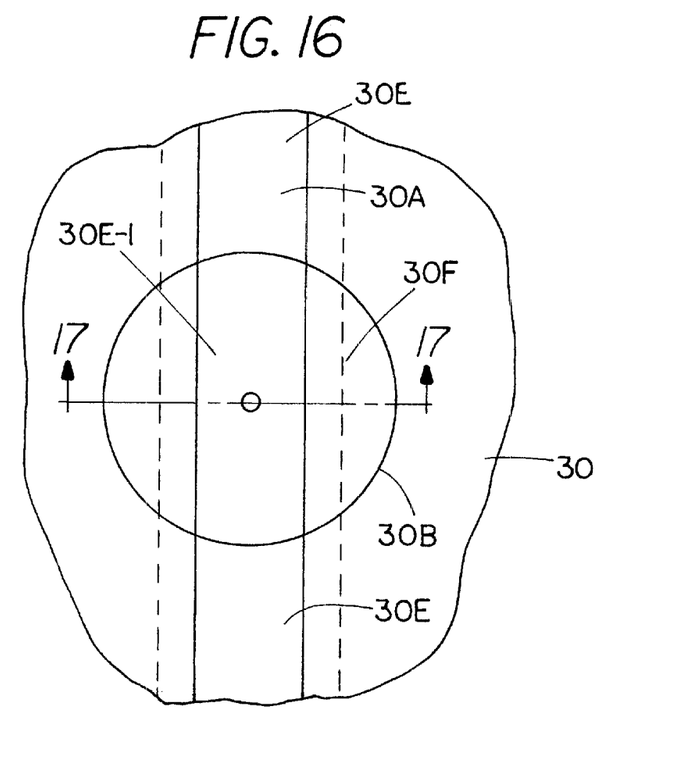
FIG. 16 is a fragmentary view of a portion of a seal plate showing a plug used for cutting seal grooves in the seal plate.
Figure 17:
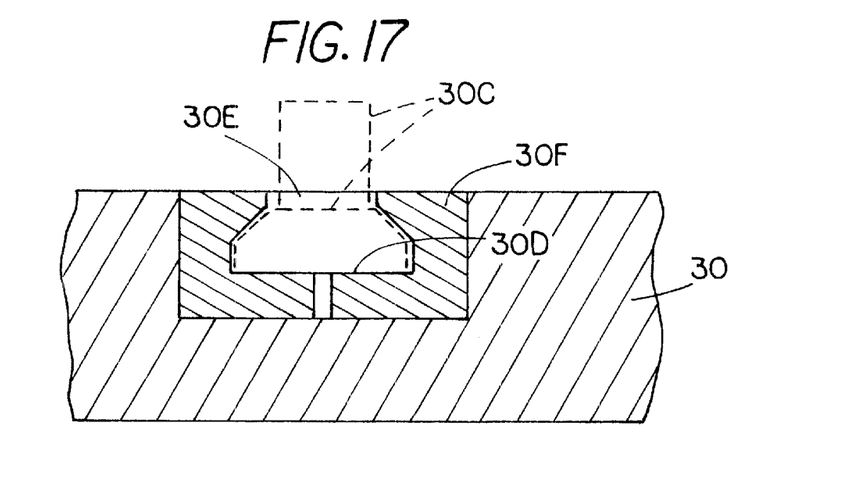
FIG. 17 is a sectional view taken as on line 17—17 in FIG. 16.

A general form of the invention illustrated in FIGS. 1 through 6 comprises an impactor assembly 10, which has a housing assembly 12, with an aerosol inlet 14 of standard size described in USP 24, Section 601. The inlet can be a standard USP type inlet tube. A pre-separator 16 is illustrated on the inlet in FIG. 1, and it is used to separate out large particles.

The aerosol that is passed through the impactor 10 is an aerosol generated by a hand-held inhaler 17 or other device that may be a liquid or dry powder drug inhaler, such as those used to control asthma and similar problems. The amount of flow from each charge is small, so the internal volume of the impactor 10 must be kept low. The flow rate through the impactor will be generated in a selected manner, for example by providing a vacuum pump such as that shown at 20 on an exhaust or flow outlet opening 22 (see FIG. 2) from the impactor housing 12. This type of impactor is described in U.S. patent application Ser. No. 09/679,936, filed Oct. 5, 2000.

The impactor 10 has a lid or cover 24 that is sufficiently thick to include flow passageways on the underside. The lid or cover 24 has an opening for the inlet pipe to pass through to seal plate 30. The lid or cover 24 is hinged along one edge to a base frame 25 that has a number of egg shaped or tear drop shaped openings that receive and support tear drop shaped impactor particle collection chambers or cups as will be shown.

As shown in FIGS. 3, 4, 5 and 6 a seal plate 30 is positioned just below the cover or lid 24 and has seals in grooves on both sides to seal passageways on the underside of the cover 24 and, on the opposite or bottom side of the seal plate 30, to seal around lips of each of the impaction chambers or cups to define sealed passageways for forming the flow path. The impaction chambers or cups will be individually numbered in this description. The first cup at the inlet is shown at 34. The inlet tube 14A passes through cover 25 and is joined to the seal plate 30 and opens through an inlet opening 32 that is sealed to carry the aerosol through the seal plate 30 into a chamber or passageway 34A defined by the first impaction stage cup 34. Cup 34 fits through an opening in a cup retainer tray or frame 36. The cup 34 has a peripheral flange 34B that rests on the tray or frame 36. The cup also fits in an opening 34E in the frame 25. The tray or frame 36 is supported on the top of the base 25.

The impaction cups are tear drop shaped as shown. The bottom wall at the large end 34F of the first stage cup (and all cups) forms the impactor surface and underlies the inlet opening 32. The flange 34B of the cup 34 is sealed with a seal 34D on the seal plate and extends transversely of the impactor to a vertical passageway 38 that opens through the seal plate 30 to interface or crossover passage 40 formed on the underside of the cover 24.

FIG. 3A is a bottom view of the base, with the cups and seal plate removed, so the interstage passages on the underside of the cover 24 can be seen. The openings in the cups on the base frame 25 are designated with the cup number followed by the letter "E". The seals on the peripheral flanges of the cups follow the shape of the cup openings in frame 25 shown in FIG. 3A, and as shown in dotted lines in FIG. 3.

The crossover or interstage passageway 40 leads to a nozzle passageway or opening in seal plate 30 (FIGS. 3 and 6) having a nozzle 44 that has openings 44A of desired size, and desired number. Particles will discharge into a second stage impactor surface of a cup 46 held in an opening 46E of base 25, under nozzle 44. The tear drop shaped cup 46 has a wide end under the nozzle 44 and a narrow opposite end. The cup 46 has a flange 46B for support and defines a passageway 46A. The small end of the cup 46 aligns with a passageway or port 50 through the seal plate and opens to a tear drop shaped passageway 54 in the cover 24.

The large end 54B of passageway 54 overlies an opening in seal plate 30 which holds a nozzle 56 that has openings 56A. Nozzle 56 overlies a tear drop shaped cup 58. The openings 56A are smaller and greater in number than the openings 44A, and the nozzle openings decrease in size in the impactor stages to the outlet. The third stage impactor cup 58 has a flange 58B and forms a passageway 58A (see FIGS. 3, 3A and 5) that opens to a vertical passageway 60 in seal plate 30 and to a passageway 62 in the cover 24. That in turn connects to a nozzle 64 that discharges into a cup 66 that fits in an opening 66E in base frame 25.

A passageway 64A that extends laterally opens through a port 68 in seal plate 30 and connects to a tear drop shaped passageway 70 in the cover 24 which directs flow through a nozzle 72.

A cup 74 with a flange 74B provides a fifth stage impactor and underlies the nozzle 72 and receives particles discharged through the nozzle 72. The cup 74 also forms a passageway 74A leading to an opening 76 and to a passageway 78 in the underside of cover 24. Cup 74 fits in opening 74E in the base, shown in FIG. 3A. Cups 66 and 74 are also shown in FIG. 1, where the impactor cover and seal plate are broken away.

The crossover passageway 78 carries flow to a nozzle 80, with openings 80A, so flow goes downwardly into an underlying sixth stage impactor cup 82 supported with a flange 82B. The cup 82 forms an impaction plate and provides a passageway 82A. Passageway 82A leads to an opening 84 and then to a passageway 86 in the underside of cover 24.

The passageway 86 leads to a nozzle 88 that has openings 88A that open to an underlying cup 90 forming a seventh impaction stage. The cup 90 is supported on a flange 90B in an opening 90E in the base frame 25 and forms a passageway 90A that leads through an opening 92 to a passageway 94 in the cover 24.

The passageway 94 opens to a final stage micro orifice filter nozzle 96. The micro orifice filter nozzle 96 discharges the flow into an underlying cup 98 with a support flange 98B that opens through bore 98G to a fluid flow outlet passage 98F in the cover 24. The passage 98F is a short cross over passageway that opens downwardly through a bore 98H to the outlet bore 22 in the base 25. A fitting 22B connects to a suitable flow line, the passageway 98F is sealed with an oval "O" ring 98J, as shown in FIG. 3. The seal plate 30, as shown, and as was explained, has "O" ring type seals on one side to seal the passageways in the cover 24 and on the other side to seal on the impactor cup flanges. The seal on the bore 98H on the bottom of seal plate 30, shown at 98K is sealed on a raised boss 25K on the base which raises the surface of the base to be level with the top of the cup flanges.

The passageways in the cover that connect between nozzles are all sealed with tear drop shaped O-ring seals. Passageways 40, 54, 62, 70, 78, 86, and 94 are sealed with seals 40A, 54A, 62A, 70A, 78A, 86A, and 94A, respectively. The flanges on the impactor cups are also sealed with tear drop shaped seals. In addition to the seal 34D, the cups 46, 58, 66, 74, 82, 90, and 98, are sealed with seals 46D, 58D, 66D, 74D, 82D, 90D, and 98D, respectively.

The "O" rings that are used for the seals shown above, are all mounted in a standard NGI "O" ring groove, that is trapezoidal shape and has a narrower opening on the exposed surface of the seal plate 30, in which the groove is formed than the base portion of the groove. Getting a cutting tool into the seal plate to form this type of an enclosed continuous groove that follows the outline of any of the seals around the openings is formed as shown in FIGS. 16 and 17 by providing a flat bottom bore 30B in the seal plate 30 that is of desired size. The bore is of large enough size to permit the tool from it is used for cutting the widest portion of the "O" ring groove to enter the seal plate. In FIG. 16, a fragmentary portion of the seal plate showing a typical "O" ring groove 30A is illustrated. The bore 30B is greater than the maximum width of the bottom 30D of the groove, which is shown in FIG. 17. The bottom surface of the groove 30D is wider than the groove opening 30E. However, the bore or opening 30B is large enough to permit the tool shown in dotted lines at 30C to be inserted into this bore 30B and then cut the continuous groove around the passageways 40, 54, 62 and the like. The "O" ring grooves are designed to provide "O" rings that seal on the flanges of the impactor cups.

The bore 30B of course, would provide a problem for sealing, but in this instance, a plug 30F that has the "O" ring groove shown in FIG. 17 formed therein is inserted in the bore 30B after the main groove has been cut. The opening 30E-1 in the plug 30F is made to align with the openings 30E of the "O" ring groove that has been formed, so that a continuous seal is maintained, and that a seal is adequately supported. The plug 30F can be press fitted into place, or can be held in other suitable ways. The bore 30B extends only partially through the seal plate 30.

The ability to mill with a suitable tool that is shown in dotted lines in FIG. 17, permits rapid formation of the "O" ring grooves that are necessary.

The cover 24 is hinged to the base with a pins that are fixed on the base and extend upwardly therefrom. The hinge members comprise two upright hinge posts 100, that are spaced apart and are part of the base or bottom frame 25. The posts are adjacent the opposite ends of the base frame. The upright posts 100 carry fixed dowel pins 100A, that are oriented on the same sides of the upright posts 100. The cover 24 has a pair of laterally extending ears 101, which protrude from the rear side of the cover, and these ears have bores 102 that are sized to receive the dowel pins 100A, so that the cover can be slid laterally, and the dowel pins fitted into the bores 102. See FIG. 7 where the cover is partially on the pins 100A. The length of the pins 100A, and the width of and the space of the posts 100 are selected in relation to the space between ears 101 and stop lugs 103, so the cover can be installed only in the open position, when the ears of the cover are engaged at all with the pins 100A.

Figure 7:
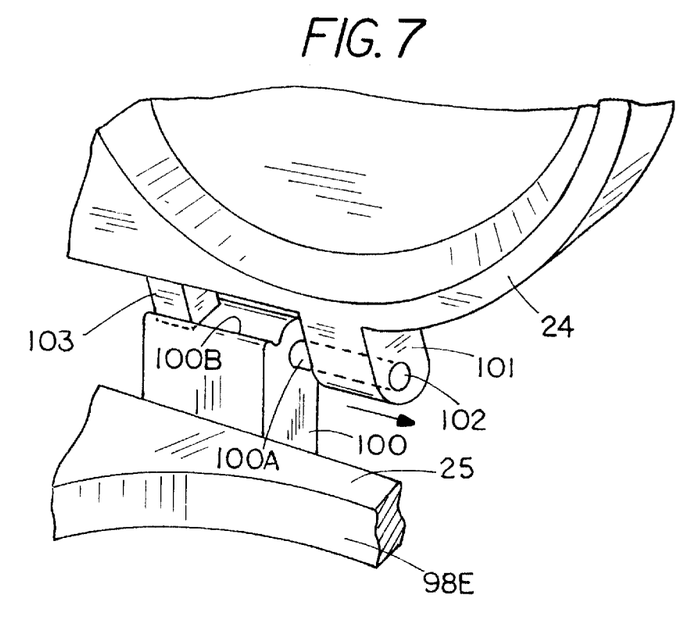
FIG. 7 is an enlarged fragmentary perspective view of the cover partially assembled on the hinge to the base.

The cover 25 also has projecting stop lugs 103 that are spaced from the ears a distance that is slightly greater than the lateral width of the associated upright post 100. The posts 100 have a small projection that forms a stop lug 100B that is positioned so that when the cover 24 is being slid on the pins 100A, as shown in FIG. 7, the lug 103 on the cover will be engaged with this projection 100B until the cover 24 is fully seated on the pins 100A with the lugs 101 up against the side surface of the respective post 100. Then the cover 24 can be closed, but until that time there is an interference, so that the cover 24 will not be closable until the recesses in the cover are aligned with the seals on the seal plate to insure that the passages and cups will be sealed.

Figure 8:
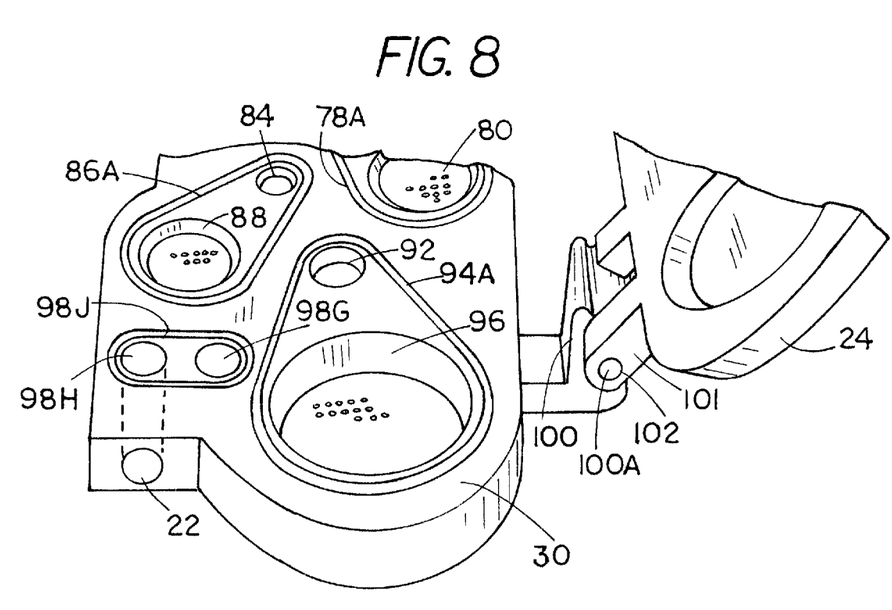
FIG. 8 is a perspective view of the discharge end of the impactor, with the cover in an open position to show a portion of a seal plate.

In other words, the cover 24 will be maintained in its open position as shown schematically in FIGS. 7 and 8 until the lugs 103 have cleared the posts 100, which gives the correct position for sealing on the "O" rings.

The movable parts of the latch assembly are also maintained on the bottom frame only, and as can be seen in FIGS. 1, 2, 3 and 11, the bottom frame 25 has a pair of ears 104A and 104B near each end, and these ears in turn are provided with a pin opening for pivotally mounting handle links 105A on pins 105C. The handle links 105A are connected together with a cross handle 105C. The handle links will move about the pin. A separate latch link 106 is mounted along the inner sides of the handle links 105A between the ears 104B and the respective handle link 105A.

Figure 9:
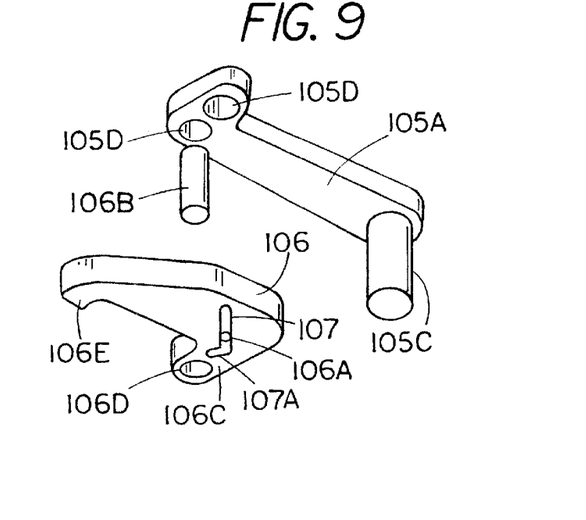
FIG. 9 is a fragmentary perspective view of a latch assembly, including a latch plate and handle plate in an exploded view.

The ears 104B each mount a fixed cam pin 106A in openings in the ears. The cam pins 106A protrude into the space between the ears 104A and 104B of each pair, but extend only a short distance so it will fit into and slide along cam slots 107 on each of the latch links 106. The latch links 106 have bores 106D that support fixed pins 106B that extend laterally toward the associate handle link (see FIGS. 9 and 10) and which are rotatably mounted in a bore 105D of the associated handle link. The handle link has a crank arm 105F and the bore 105D is in the crank arms so it is offset from the pivot pin 105B. The distance between pins 105B and bores 105D acts as a crank arm when the handle links 105A are pivoted on pins 105B. The pins 106B of the latch links then act as crank pins and will move the end sections 106C of latch links 106. The path of movement of the latch links 106 is defined by the cam pins 106A traveling in cam slots 107 on one side of the latch links 106. The cam slots 107 have a long angled section 107B that has a low end 107C, and a short section 107A that extends upwardly at an angle from the low point 107C. The low point 107C forms a junction between cam slot section 107A and cam slot section 107B. The latch links 106 have hook ends 106E that will fit over cross pins 108 that are supported on and extend between the ears 109 on the cover 24.

Figure 1:
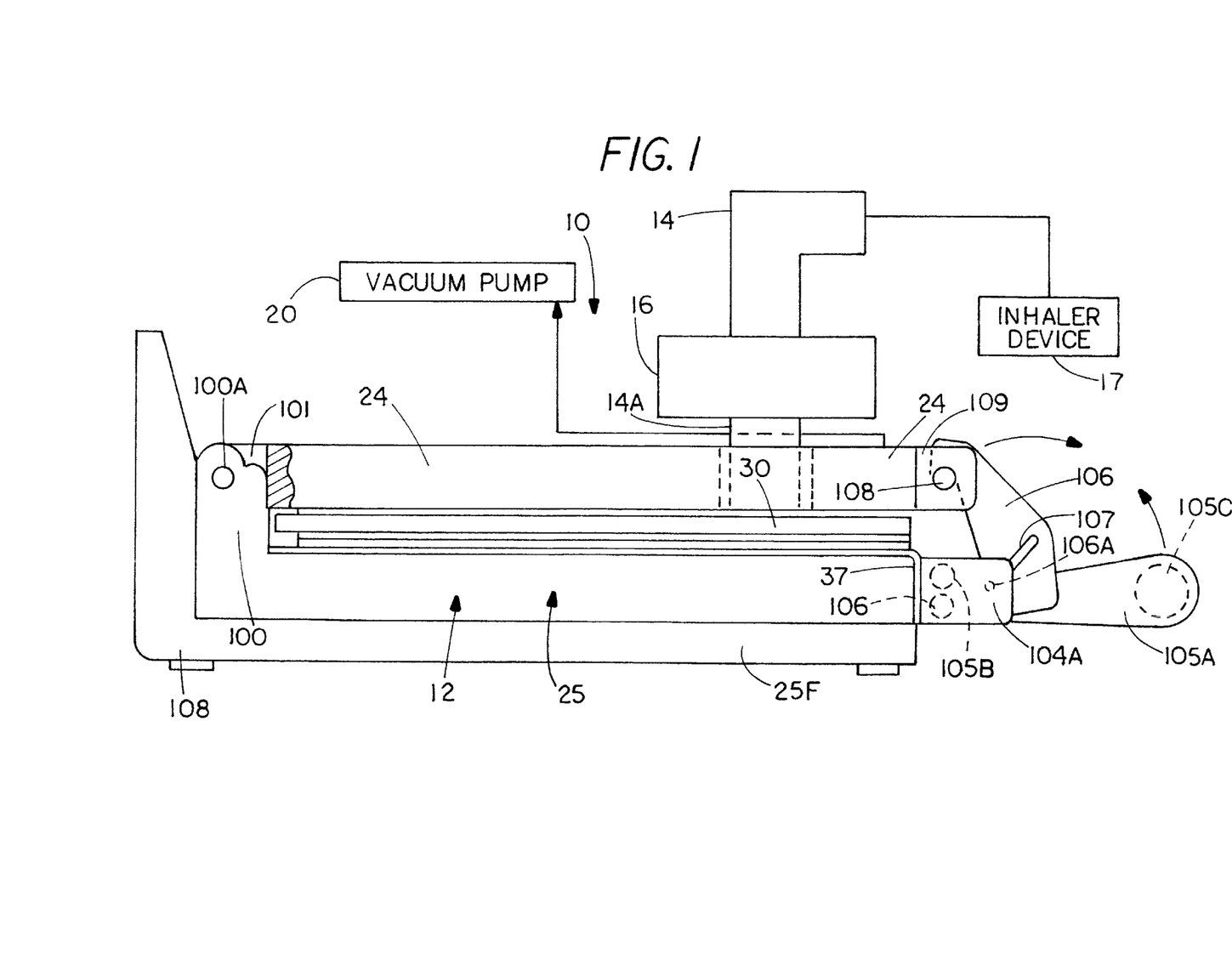
FIG. 1 is a side view of an impactor made according to the present invention.
Figure 2:
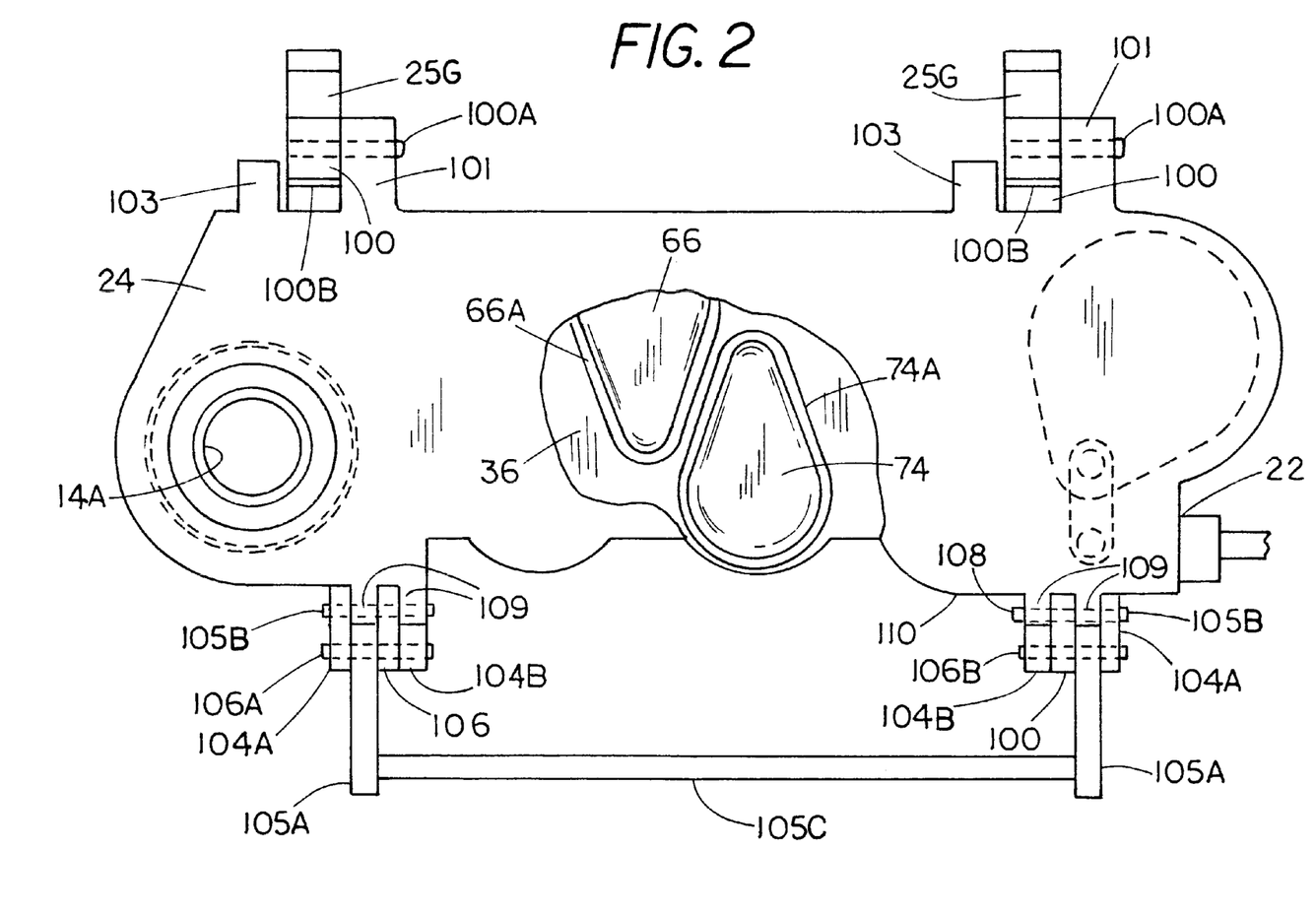
FIG. 2 is a top plan view thereof with parts broken away.
Figure 10:
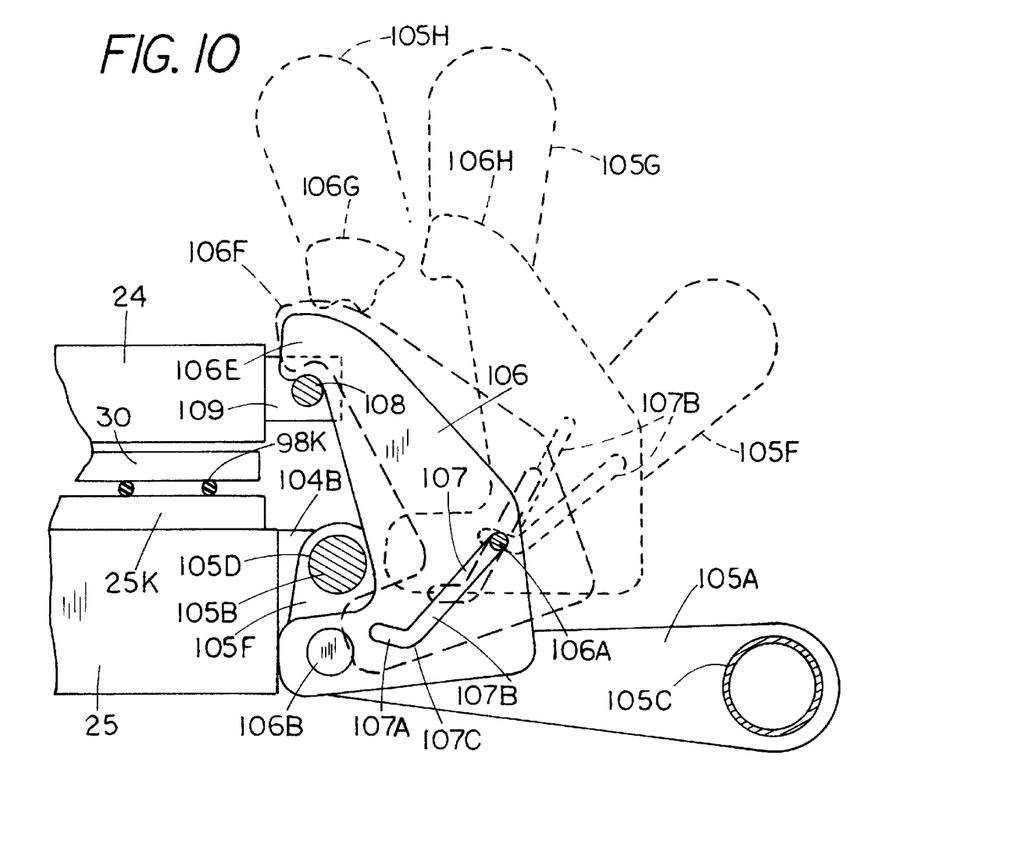
FIG. 10 is a side elevational view of right hand latch links and latch lever shown in position for latching and releasing the cover in place on the base.

When the latch handle assembly 105 is moved to its latching position, which is the lowered position shown in FIGS. 1 and 10, the cam pins 106A are in the upper ends of the slots section 107B and the pins 105D and 106B go slightly over center, which provides a detend position. The latch hooks 106E are clamped against the pins 108 to securely latch the cover 24 in place, compressing the O-ring seals.

When unlatching the handle bar 105C is raised or moved counterclockwise in FIGS. 1 and 10. The movement of the latch link starts to raise pin 106B and the cam pins 106B slide along the cam slot section 107B. This causes the latch hooks 106D to move up and away from the cross pins 108, to release the cover as shown at positions 106F and 105F in dotted lines in FIG. 10. Continued movement of the latch handle 105C counterclockwise will cause the cam pins 106A to move in the slot sections 107B and toward low point 107C and move the latch links 106 upwardly to the position as shown at position 106G and 105G. The cam pin is then in the low point 107C, the handle 105 moves through a substantial arc and the latch link primarily raises. The last portion of movement of latch handle 105 causes the latch link to move so cam pin 106A moves into the cam slot section 107A, which moves the latch link rapidly away from the cover, as shown by position 106H and 105H in FIG. 10. The cover 24 can be opened.

The cam section 107C lifts the latch link hook section 106E away from the pin 108, so that the cover is released. When clamped down, a very secure, tight seal is obtained by compressing the O-ring seals on seal plate 30.

As shown in FIG. 1, the base 25 has support brackets 25F that have upright arms 25G that will support the impactor assembly 10 with the hinge edge downwardly, letting it stand in an upright position with the handle side extended upwardly.

The bottoms of the impactor cups can be supported so they clear the supporting surface. This means that when the cover 24 is opened, after the test has been run, tray 36 can be lifted out of the bottom frame, manually or with a fixture. When the tray is lifted all of the impactor cups are removed as a unit. The cups may be placed either in a separate container and sealed, or otherwise processed for recovering and analyzing the particles in each impactor cup.

Figure 3:
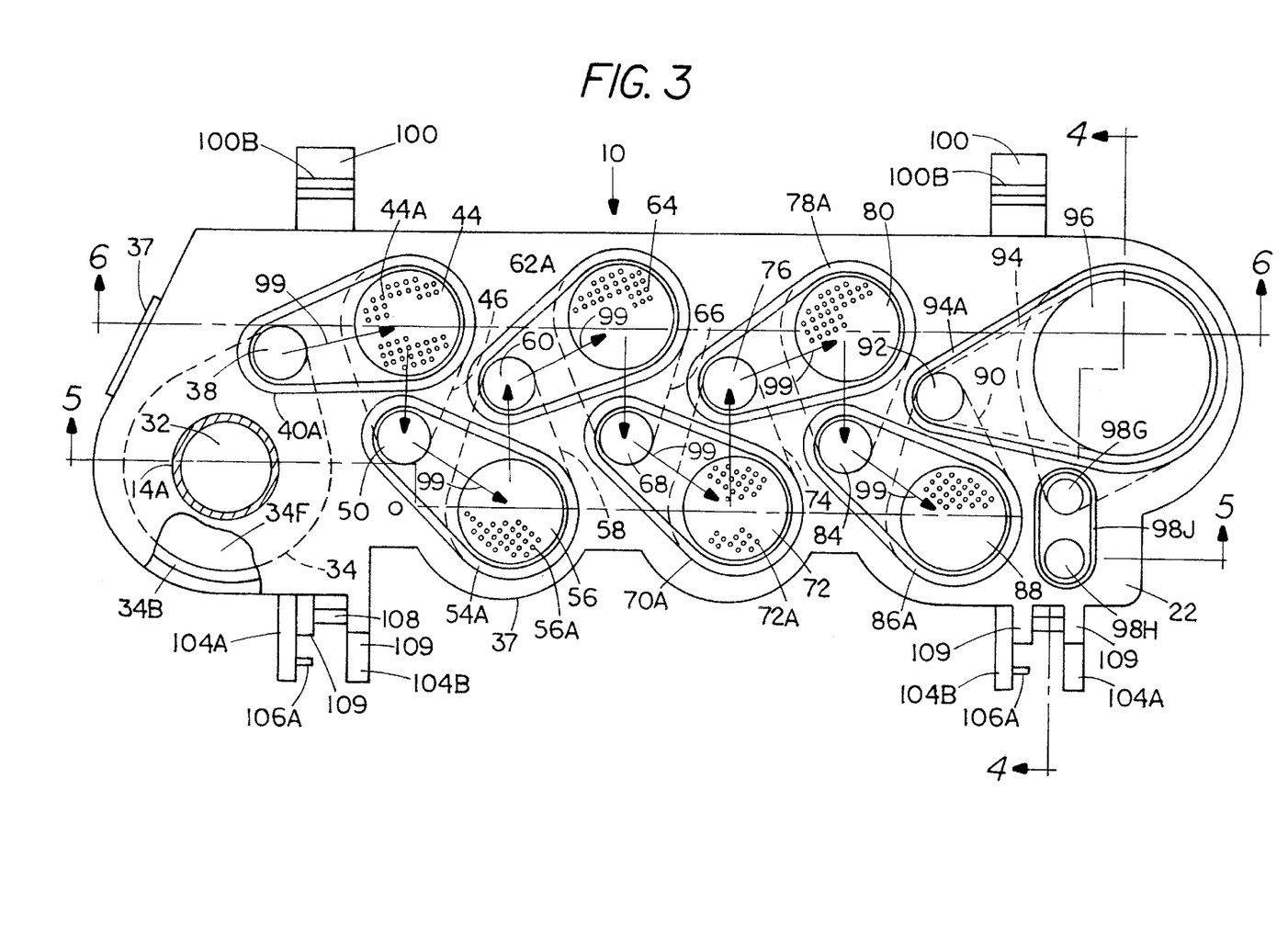
FIG. 3 is a top plan view thereof with the top cover removed.
Figure 3A:
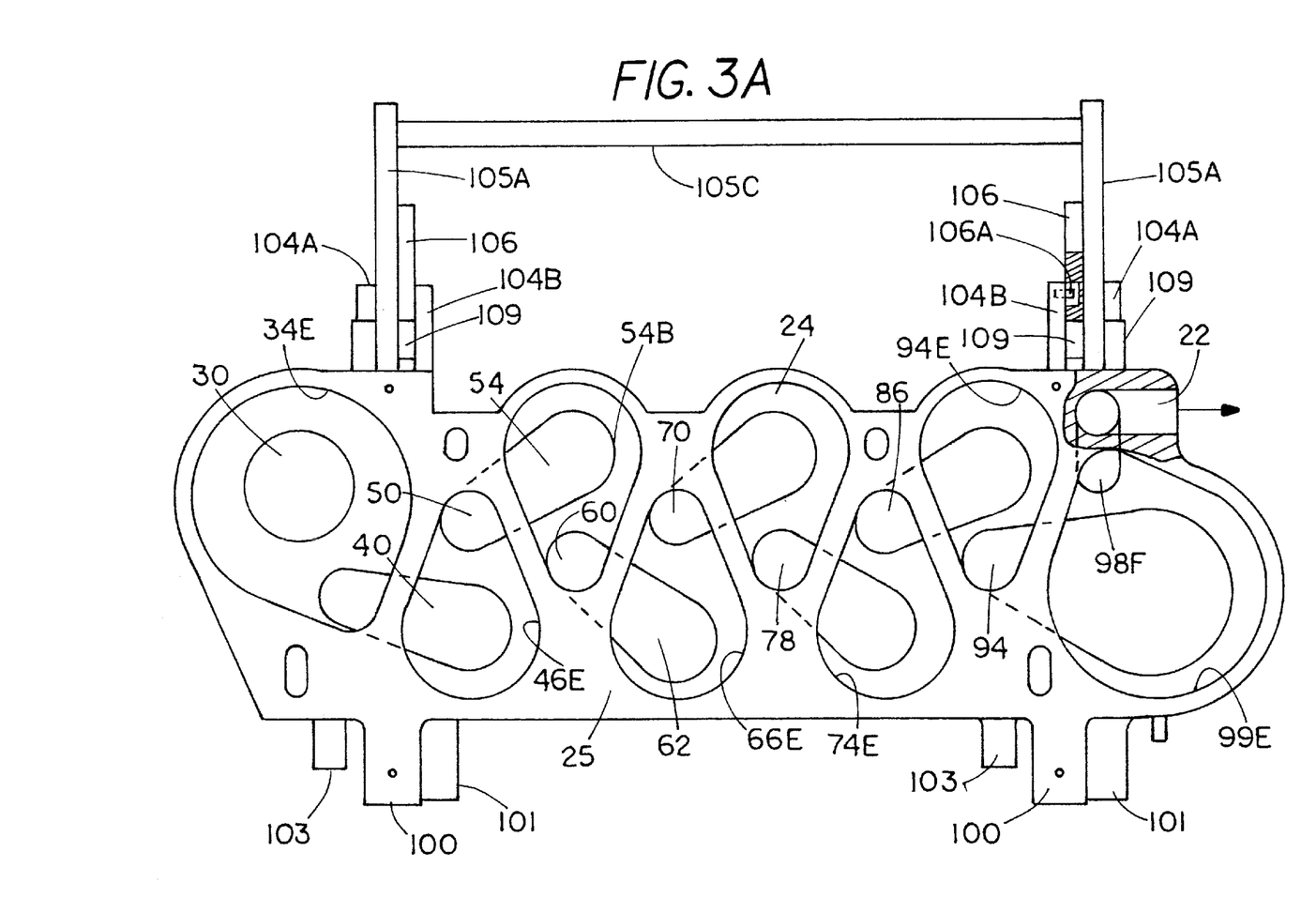
FIG. 3A is a bottom plan view with cups and a seal plate removed to show interstage passages on the underside of a cover.
Figure 4:
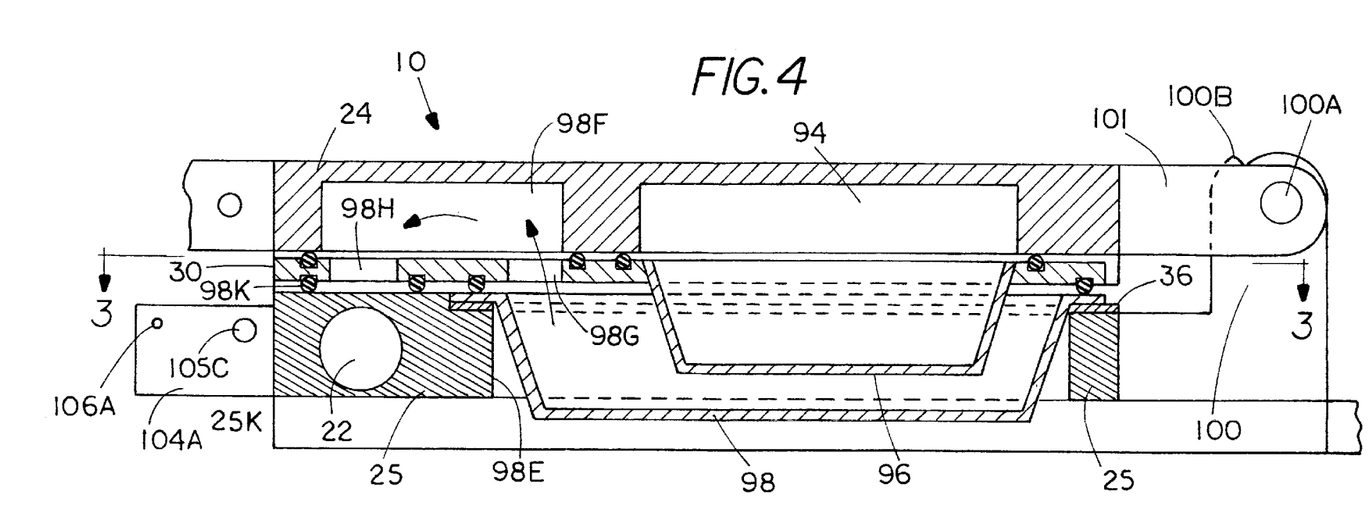
FIG. 4 is a sectional view taken as on line 4—4 in FIG. 3.
Figure 5:
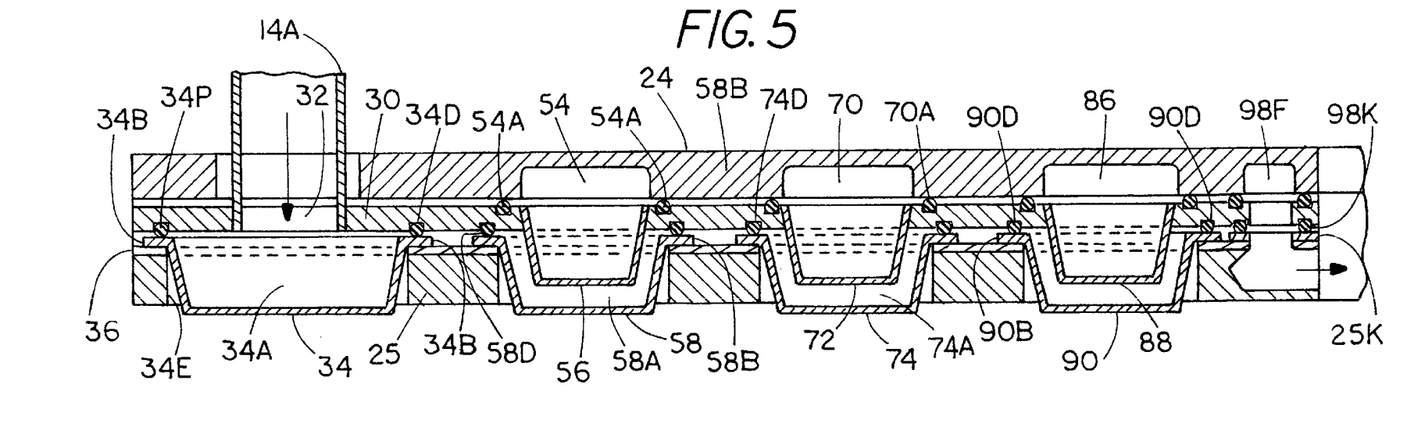
FIG. 5 is a sectional view taken as on line 5—5 in FIG. 3.

The flow paths through the impactor are shown essentially in FIG. 3, with arrows 99. The flow path is from the inlet to the outlet through the series of impactor nozzles or orifices.

The nozzles and the orifice sizes are selected to provide at least 5 cut points at all desired flow ranges that are between 0.4 $\mu$m and 6.0 $\mu$m. In addition, one stage should provide particles between 5 $\mu$m and 10 $\mu$m. A pressure drop across the impactor of less than 100 inches of water at the maximum flow rate is desired.

Figure 11:
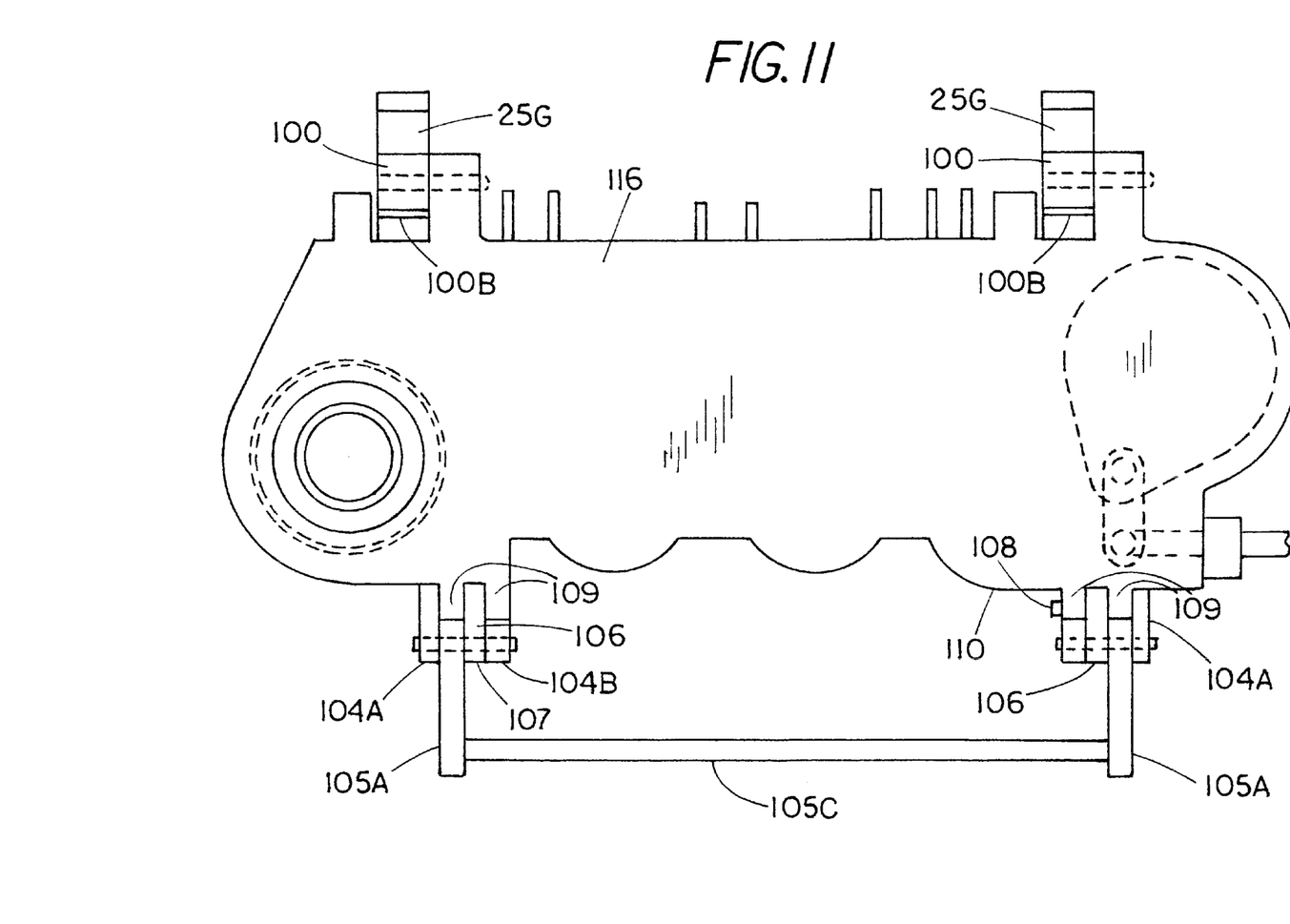
FIG. 11 is a top view of a test fixture cover in place on the base shown in FIGS. 1–10.
Figure 12:
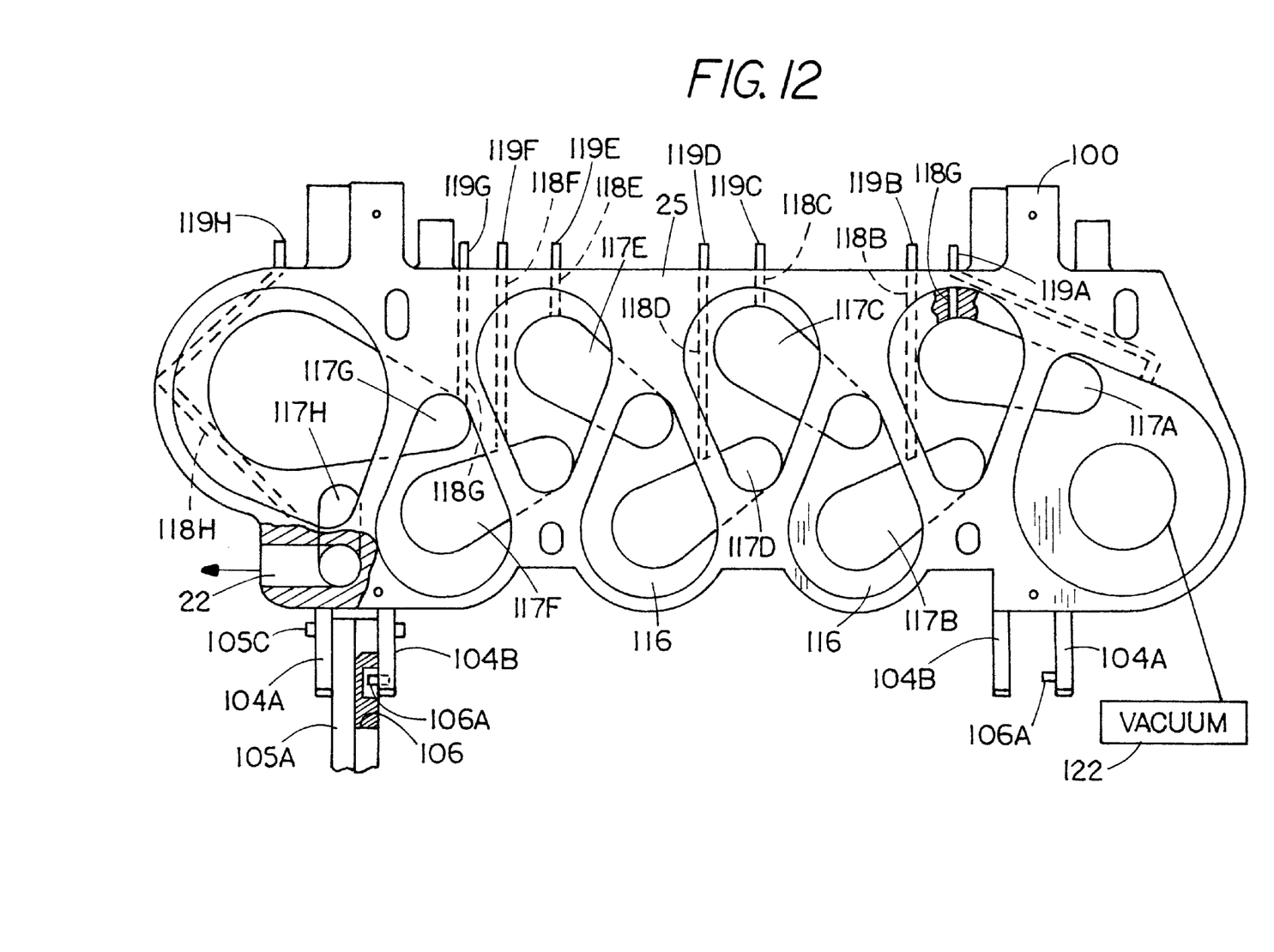
FIG. 12 is a bottom view of the test fixture of FIG. 11 with parts removed, similar to FIG. 3A, to show the passageways in the test fixture cover.

The integrity or continued accuracy of the nozzle or orifice plates of the cascade impactor can be checked by measuring the differential pressure between the impactor nozzles, as was stated, and in order to do that, a test cover indicated generally at 116 is placed onto the base shown in top view in FIG. 11 and in bottom view in FIG. 12, with the base frame in place. The O-ring seals are maintained on the seal plate, and the test cover is placed over the "O" rings and nozzles and overlies the arrangement shown in FIG. 3. The test cover 116 has recesses that replicate the recesses in the cover 24 that is used for the regular impactor flow. These recesses are shown in FIG. 12 at 117A through 117G. The exhaust passageway is shown at 121 in FIG. 14. The test cover 116 has a separate passageway or bore 118A–118G open to each of the recesses 117A–117G in the cover and a separate passageway 118H opens to the exhaust passageway 117H in the cover, which corresponds to passageway 98F. Each of the passageways 118A and 118G, in turn are connected to a tube fitting shown generally at 119A–119H. The passageways shown at 118A–118H are thus open to the individual recesses, and the exhaust passageway 121. The pressure in the passageways can be sensed by a series of pressure sensors in a housing. These sensors are indicated at 120A—120A. The sensors provide electrical inputs to a computer 134. The sensor output can be arranged to provide absolute pressure at each passageway, differential pressures across each adjacent pair of nozzle or orifice plates. A standard rate of flow is established, for example, 100 L/min and the measurements taken. By periodically placing the test cover 116 on the impactor base and checking the pressure differentials can be obtained to check to see if plugging or wear is occurring.

Figure 13:
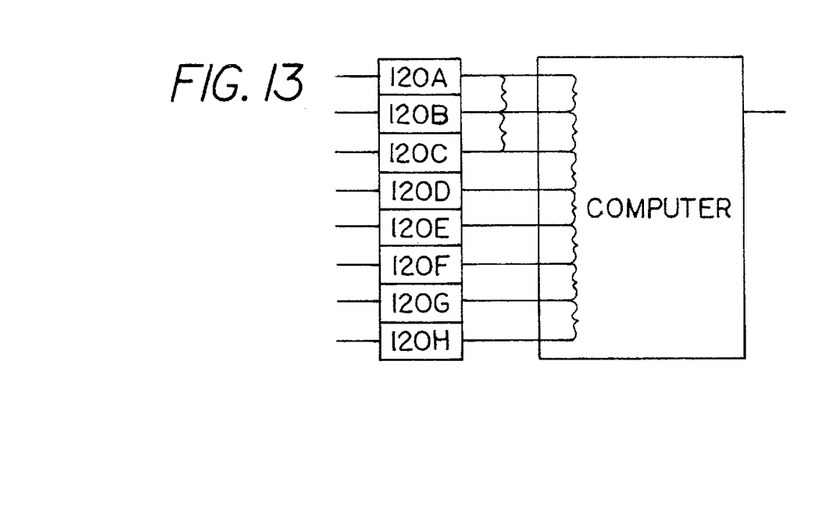
FIG. 13 is a schematic representation of pressure sensors used with the test fixture of claim 11.

A schematic representation is shown in FIG. 13 of the pressure sensors. The sensors provide signals to the computer 134. If desired differential pressure sensors can be provided for direct measurement of pressure differentials.

By properly using the signals from the sensors, the computer will provide differential pressure across each of the nozzle or orifice plates. The overall pressure drop can be obtained between the inlet and the outlet. This will permit determining the operational characteristics of the impactor plates and permit calculation of flow rates. Computer 134 does the calculations, and can be used to provide alarms, and to adjust flows, if desired.

In order to carry out the present tests, it must be certain that the test cover is sealed properly. A vacuum source 122 is connected to the inlet and since the other fittings are connected to pressure sensors, closing the outlet with a valve will close the system. Any leak down of the vacuum indicates a bad seal. Vacuum is applied to the openings, to insure that the seals are tight. Such a vacuum can be applied with a simplified fixture as shown in co-pending application Ser. No. 09/733,115, filed on Dec. 8, 2000, and entitled LOW VOLUME VACUUM LEAK TEST FIXTURE. Other sources of vacuum also can be used.

Making sure that all of the seals are sealed is necessary for determining the flow rate through the impactor. A flow meter can be included in the housing for the computer. The flow is a function of the pressure drop across the impactor, so the pressure sensors also can be used for calculating flow.

Figure 6:
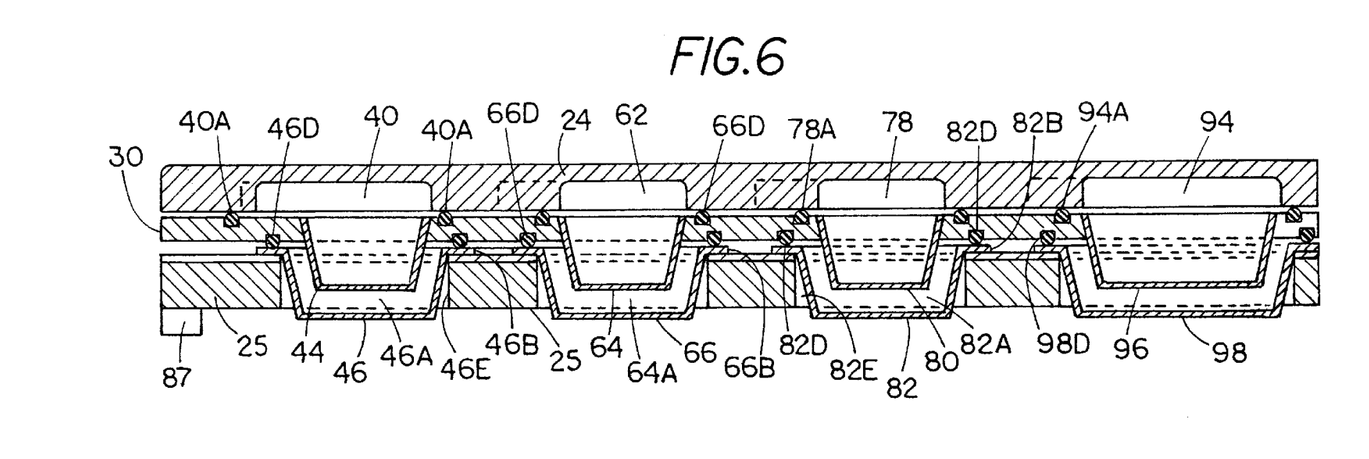
FIG. 6 is a sectional view taken as on line 6—6 in FIG. 3.
Figure 14:
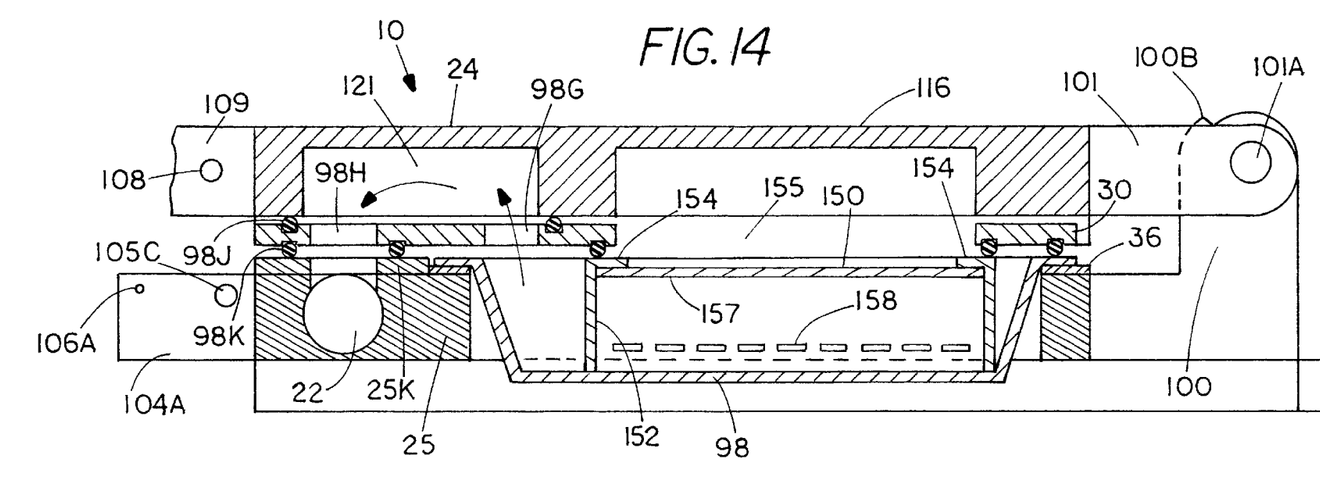
FIG. 14 is a section view similar to FIG. 4 showing a modified discharge arrangement utilizing a final filter.
Figure 15:
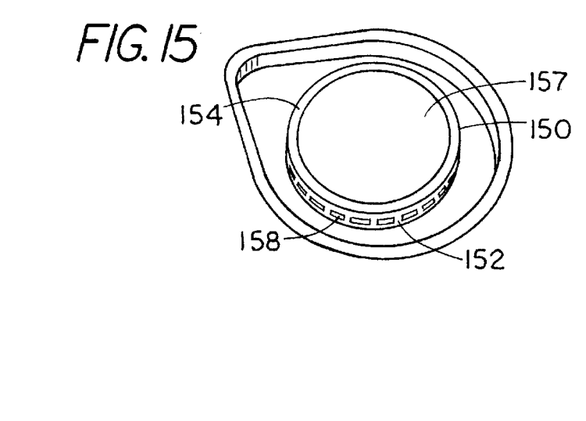
FIG. 15 is a perspective view of the final filter shown in FIG. 14.

FIGS. 14 and 15 show a final filter assembly 150 that may be placed in the final impactor cup 98, and replacing the filter plate 96 shown in FIG. 6. The showing is with test cover 116 in place, but cover 24 would be used for classification operations. The final filter 150 is an inverted cup having a peripheral bounding wall 152, and an inwardly turned flange 154 that defines an open space 155 that is covered with a fine screen forming a final filter 157. The peripheral wall 152 has a series of apertures or openings therein indicated at 158, and as can be seen, the edges of the peripheral wall 152 rest on the upper surface of the impactor cup 98. The final filter then filters the fluid coming through the impactor. At this stage, very few particles remain, particularly in drug inhalation devices, and the filter will provide for clean airflow out through the exhaust openings as indicated by the arrows in FIG. 14. The screen 157 can have a desired mesh, or it can be a perforated screen of very thin material, as desired.

The openings 158 are provided in sufficient number and in sufficient size so that the back pressure is not affected adversely.

Figure 18:
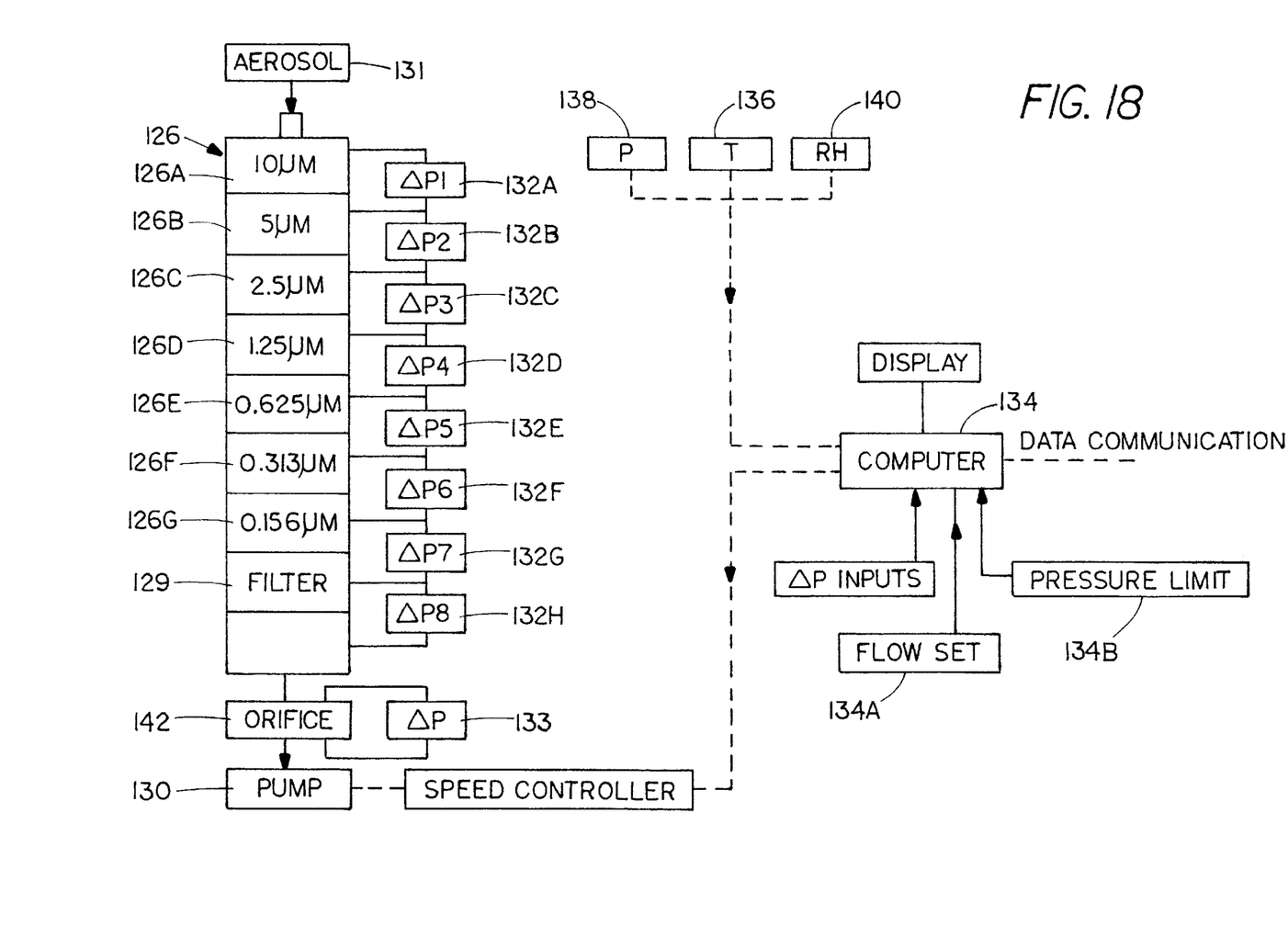
FIG. 18 is a schematic representation of a vertically stacked cascade impactor having differential pressure measurements made according to the present invention.

FIG. 18 is a schematic diagram of a prior art cascade impactor 126 that also is shown to illustrate sensing differential pressures between impactor stages. The impactor stages 128A–128G provide particle size cutoff points as shown at desired sizes, based on the nozzle or orifice size. A filter 129 is used at the outlet. A pump 130 provides the flow of aerosol through the cascade impactor 126 from an aerosol source 131. The pressure differential between adjacent stages is measured by differential pressure sensors 132A–132G, which are used to measure the pressure drop across each impactor stage. A sensor 132A measures the pressure drop across filter 129. Alternatively, some adjacent impactor stages can be combined and the pressure drop across a group of stages can be measured with a single sensor. The pressure sensor outputs are also provided to a computer 134.

Ambient temperature can be sensed with a temperature sensor 136. Barometer pressure is sensed with a sensor 138; relative humidity can be sensed with a sensor 140. Flow rate can be sensed by calculating the flow based on measured pressure drop across an orifice plate 142 or across the entire cascade impactor, that is between the inlet and the outlet. A separate flow sensor can be used. The sensors are connected to the computer 134 for signal processing and recording.

The computer 134 can also generate an electrical signal based on the sensor inputs to adjust the flow by controlling the speed of pump 130 with a speed controller to one of several preset values.

The pressure drop across each impactor stage in both forms of the impactors shown can be sensed by the individual pressure sensors and compared with standard or reference values which may be obtained by calibration at the factory or at user's standard calibration laboratory at periodic intervals.

During use in the field, when particles begin to accumulate on the small nozzles or orifices in the nozzle plates, the pressure drop across the nozzle or orifice plates increases. This increase can be detected. In addition, any leak in the system, damage to the nozzle plates due to cleaning or other causes, as well as a mistake in the assembly and operation of the impactor can also be detected automatically.

Preset pressure limits can be established so that when the pressure difference between the measured value during use and the calibrated set point exceeds the limit, the operator will be alerted to the situation for corrective actions. The data can also be stored in the computer memory from a flow set control 134A and a pressure limit controller 134B. Each pressure sensor can be individually monitored by the computer. This way, changes that have occurred during sampling can be detected and the time at which these changes have taken place will also be known. This will enable the operator to determine if the data are sufficiently accurate for use or need to be discarded.

Change in nozzle opening dimensions due to particle accumulation and blockage is generally not an issue when the nozzle is a few millimeters or more in diameter. For smaller nozzles, especially those found in modern precision impactors, it is important. Due to the very small nozzle or orifice diameter, the nozzle plate carrying these small nozzles must also be very thin, typically a few thousandth of an inch in thickness. Such thin nozzle plates can be easily damaged during ultrasonic cleaning. Presently, there is no convenient way of detecting the small change in nozzle diameter due to particle accumulation and/or damage during cleaning. Manual inspection by microscope is slow and labor intensive. Due to the high microscope magnification needed to see the small nozzles, the field of view is quite small, meaning that only a few nozzles can be seen and examined in a given field of view. Since micro-orifice nozzle plates with as many as 2,000 orifices are routinely made, and as many as 10,000 orifices may be needed in the future, the convenient and low cost method of detecting change in nozzle dimensions by sensing differential pressure accomplishes the objective automatically.

One important application of cascade impactors is to measure the size distribution of aerosols produced for medicinal uses. In such applications, the specific chemical compound, i.e. drug, is aerosolized, which is then inhaled by the patient. The most widely used devices for producing medicinal aerosols for inhalation therapy are the metered dose inhaler (MDI) and the dry-powder inhaler (DPI). These devices produce a specific quantity of drug in aerosol form with each application, usually by depressing the device with a thumb or squeezing the device between fingers to release a puff of aerosol containing the required dose which the patient then inhales.

Although the present invention has been described with reference to preferred embodiments, workers skilled in the art will recognize that changes may be made in form and detail without departing from the spirit and scope of the invention.

What is claimed is:

1. In a cascade impactor formed with a number of impaction stages, having a base for carrying an impactor cup to each stage, and a first cover member for providing sealed passageways for flow of fluid from one impactor stage to the next impactor stage in series for impacting, the improvement comprising a second test cover for mounting on said cascade impactor having passageways replicating that of the first cover, and at least a plurality of the passageways having a separate bore leading therefrom to the exterior for connection to a pressure sensor.

2. The impactor of claim 1, wherein said test cover has a substantially planar surface, the passageways being recessed into said planar surface, and said planar surface sealing on seals that define the passageways.

3. The impactor of claim 1, wherein the bores have tube connectors on the exterior of the cover, all of the tube connectors being on one edge of the test cover.

4. The impactor of claim 1, a pressure sensor to sense pressure in each bore, to provide signals indicating the pressure in each bore to determine pressure differentials between each impactor stage.

5. The impactor of claim 4, wherein each impactor stage has a nozzle plate, the pressure differentials indicating the condition of nozzles in the nozzle plate.

6. A cascade impactor comprising a plurality of individual impactor stages held on a base, each of said stages including an impactor nozzle and an impactor plate, and the stages being arranged generally side by side on the base and having sealing surfaces that are generally planar for all of the impactor stages, and an integrity checking cover member for sealing on the sealing surfaces of the impactor stages, the cover member having passageways connecting the impactor stages in series, and at least a plurality of the passageways in the cover member having a separate bore in the cover member leading to the exterior of the cover member for connection to a pressure sensor.

* * * * *